(12) United States Patent
Kwon et al.

(10) Patent No.: US 11,738,107 B2
(45) Date of Patent: Aug. 29, 2023

(54) AROMA DIFFUSING SYSTEM

(71) Applicant: DEEPSCENT INC., Daejeon (KR)

(72) Inventors: Il-bong Kwon, Seoul (KR); Ki-back Jung, Busan (KR); Ha-yan Choi, Daejeon (KR)

(73) Assignee: DEEPSCENT INC., Daejeon (KR)

( * ) Notice: Subject to any disclaimer, the term of this patent is extended or adjusted under 35 U.S.C. 154(b) by 452 days.

(21) Appl. No.: 17/045,472

(22) PCT Filed: Dec. 26, 2019

(86) PCT No.: PCT/KR2019/018461
§ 371 (c)(1),
(2) Date: Oct. 5, 2020

(87) PCT Pub. No.: WO2020/145554
PCT Pub. Date: Jul. 16, 2020

(65) Prior Publication Data
US 2021/0052762 A1  Feb. 25, 2021

(30) Foreign Application Priority Data
Jan. 8, 2019  (KR) .................. 10-2019-0002472

(51) Int. Cl.
*A61L 9/12*  (2006.01)

(52) U.S. Cl.
CPC .............. *A61L 9/125* (2013.01); *A61L 9/122* (2013.01); *A61L 2209/11* (2013.01); *A61L 2209/133* (2013.01)

(58) Field of Classification Search
CPC ...... A61L 9/125; A61L 9/122; A61L 2209/11; A61L 2209/133; A61L 9/14; A61L 2209/21; G06Q 50/10
See application file for complete search history.

(56) References Cited

U.S. PATENT DOCUMENTS

2018/0036448 A1*  2/2018  Becker ............... A61L 9/12
2021/0386898 A1*  12/2021  Sivagaminathan .... G06Q 50/00

FOREIGN PATENT DOCUMENTS

KR  10-2016-0059522 A  5/2016
KR  10-1769274 B1  8/2017
(Continued)

*Primary Examiner* — Sean E Conley
*Assistant Examiner* — Brendan A Hensel
(74) *Attorney, Agent, or Firm* — Goldilocks Zone IP Law

(57) ABSTRACT

An aroma diffusing system according to an example embodiment includes an aroma diffusing device and a mobile device. The aroma diffusing device includes a wireless communication module. The aroma diffusing device is equipped with first through n-th aroma capsules selected among a plurality of aroma capsules, which emit respective aromatic substances having different scents from each other. The mobile device is connected to the aroma diffusing device through a wireless communication. The mobile device independently controls an intensity of the emission of the aromatic substance of each of the first through n-th aroma capsules, which are installed in the aroma diffusing device, to determine a combination of scents diffused from the aroma diffusing device. The mobile device controls the intensity of the emission of the aromatic substance of each of the first through n-th aroma capsules by digitizing the intensity to an integer value.

12 Claims, 8 Drawing Sheets

(56) References Cited

FOREIGN PATENT DOCUMENTS

| KR | 10-2017-0103706 A | 9/2017 |
| KR | 10-2018-0055806 A | 5/2018 |
| KR | 10-2018-0072933 A | 7/2018 |

* cited by examiner

AROMA DIFFUSING SYSTEM

CROSS-REFERENCE TO RELATED APPLICATIONS

This application claims the benefit under 35 U.S.C. Section 371, of PCT International Application No. PCT/KR2019/018461, filed on Dec. 26, 2019, which claimed priority to Korean Patent Application No. KR 10-2019-0002472, filed on Jan. 8, 2019, the disclosures of which are hereby incorporated by the references.

TECHNICAL FIELD

Example embodiments relate to an aroma diffusing system, and more particularly to an aroma diffusing system that diffuses various combinations of scents under a control of a mobile device.

BACKGROUND ART

Generally, an aroma device exhilarates people by diffusing an aromatic substance having a good scent.

Passive aroma devices that passively diffuse aromatic substances in a liquid state or a solid state and active aroma devices that actively diffuse aromatic substances are commercialized.

However, conventional aroma devices automatically diffuse aromatic substances periodically or diffuse aromatic substances based on a detection of a surrounding environment.

Therefore, conventional aroma devices are hard to control a kind and an intensity of scents based on a user's preference.

DISCLOSURE OF INVENTION

Technical Problem

Example embodiments are to solve the problems of the conventional technology, and more particularly to provide an aroma diffusing system that is capable of diffusing various combinations of scents based on a user's preference.

Solution to Problem

Some example embodiments are directed to provide an aroma diffusing system. The aroma diffusing system includes an aroma diffusing device and a mobile device. The aroma diffusing device includes a wireless communication module. The aroma diffusing device is equipped with first through n-th aroma capsules selected among a plurality of aroma capsules, which emit respective aromatic substances having different scents from each other. Here, n represents an integer equal to or greater than two. The mobile device is connected to the aroma diffusing device through a wireless communication. The mobile device independently controls an intensity of the emission of the aromatic substance of each of the first through n-th aroma capsules, which are installed in the aroma diffusing device, to determine a combination of scents diffused from the aroma diffusing device. The mobile device controls the intensity of the emission of the aromatic substance of each of the first through n-th aroma capsules by digitizing the intensity to an integer value.

Advantageous Effects of Invention

According to example embodiments, the aroma diffusing system may store the combination of scents that the user prefers and provide the same combination of scents as before by selecting one of the stored scents, such that the aroma diffusing system may provide an increased convenience to the user.

According to example embodiments, the user may share the combination of scents that the user wants to share with other users and enjoy the shared scents that are shared by the other users easily using the aroma diffusing system, such that the aroma diffusing system may provide an increased satisfaction to the user.

BEST MODE FOR CARRYING OUT THE INVENTION

Figure 1:
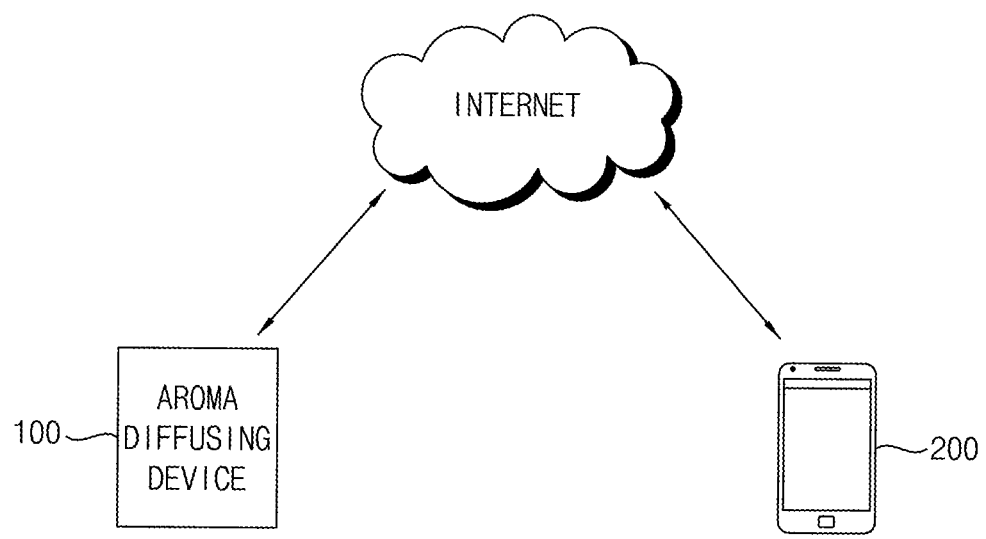
FIG. 1 is a diagram illustrating an aroma diffusing system according to example embodiments.

Various example embodiments will be described more fully with reference to the accompanying drawings, in which some example embodiments are shown. The present inventive concept may, however, be embodied in many different forms and should not be construed as limited to the embodiments set forth herein. Rather, these embodiments are provided so that this disclosure will be thorough and complete, and will fully convey the scope of the present inventive concept to those skilled in the art. Like reference numerals refer to like elements throughout this application.

It will be understood that, although the terms first, second, etc. may be used herein to describe various elements, these elements should not be limited by these terms. These terms are used to distinguish one element from another. For example, a first element could be termed a second element, and, similarly, a second element could be termed a first element, without departing from the scope of the present inventive concept. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments and is not intended to be limiting of the inventive concept. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, various example embodiments will be described with reference to the accompanying drawings.

FIG. 1 is a diagram illustrating an aroma diffusing system according to example embodiments.

Referring to FIG. 1, an aroma diffusing system 10 includes an aroma diffusing device 100 and a mobile device 200.

The aroma diffusing device 100 may include a wireless communication module. The aroma diffusing device 100 may communicate with the mobile device 200 through a wireless communication using the wireless communication module.

As illustrated in FIG. 1, the wireless communication may correspond to an internet. In this case, the wireless communication module included in the aroma diffusing device 100 may correspond to a Wi-Fi communication module, and the aroma diffusing device 100 may be connected to the internet through an external wireless access point (AP) to communicate with the mobile device 200.

However, example embodiments are not limited thereto. According to example embodiments, the wireless communication may include various kinds of wireless communications. For example, the wireless communication may correspond to a Bluetooth communication. In this case, the wireless communication module included in the aroma diffusing device 100 may correspond to a Bluetooth communication module, and the aroma diffusing device 100 may be directly connected to the mobile device 200 using the Bluetooth communication module to communicate with the mobile device 200.

Although the mobile device 200 is illustrated as a smart phone in FIG. 1, example embodiments are not limited thereto. According to example embodiments, the mobile device 200 may be any mobile device, such as a tablet computer, a mobile phone, a personal digital assistant (PDA), a laptop computer, etc.

Figure 2:
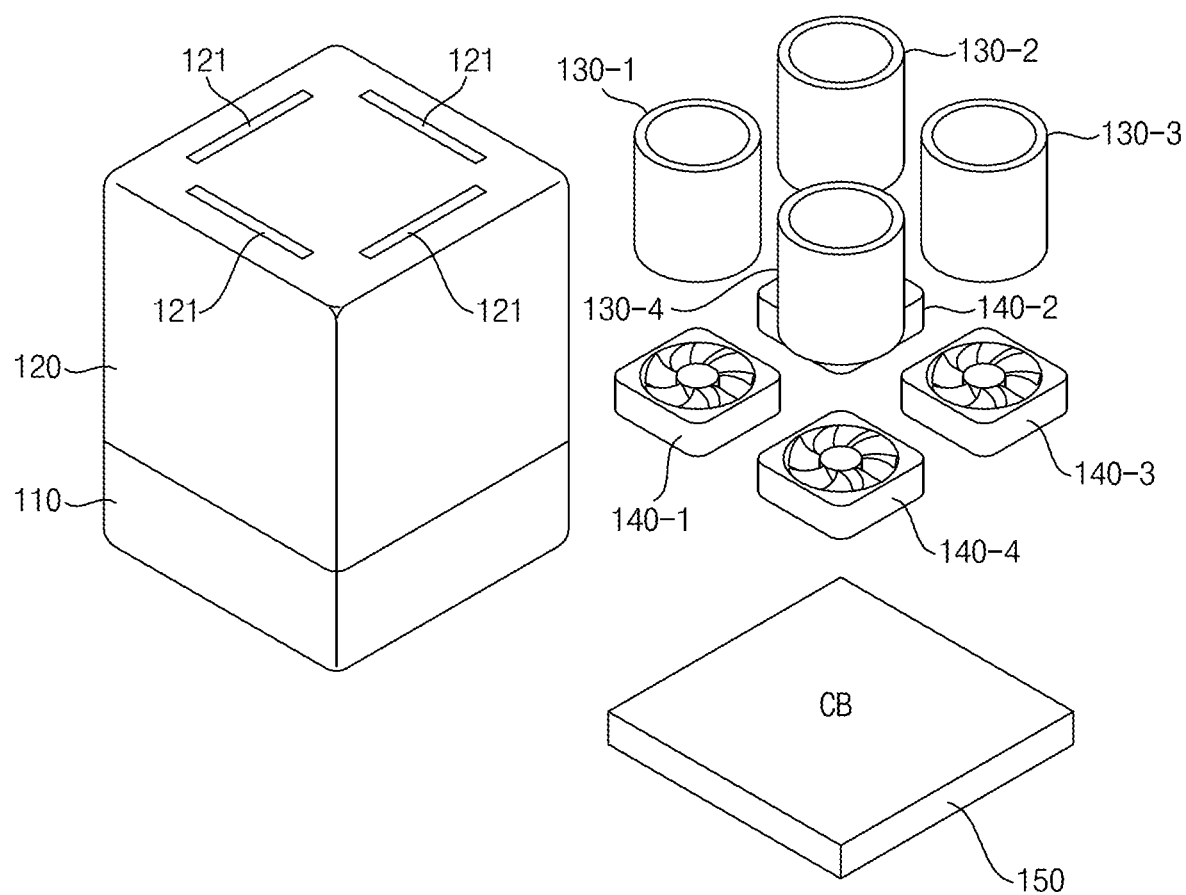
FIG. 2 is a diagram illustrating an example of an aroma diffusing device included in the aroma diffusing system of FIG. 1.

FIG. 2 is a diagram illustrating an example of an aroma diffusing device included in the aroma diffusing system of FIG. 1.

Referring to FIG. 2, the aroma diffusing device 100 may include a main body 110 and a housing 120.

In addition, the aroma diffusing device 100 may include first through n-th aroma capsules 130-1, 130-2, 130-3, and 130-4 that are installed on the main body 110 inside the housing 120. Here, n represents an integer equal to or greater than two.

The first through n-th aroma capsules 130-1, 130-2, 130-3, and 130-4 may emit respective aromatic substances having different scents from each other.

For example, a user may select n aroma capsules among a plurality of aroma capsules, which emit respective aromatic substances having different scents from each other, and the selected n aroma capsules may be installed on the main body 110 inside the housing 120 as the first through n-th aroma capsules 130-1, 130-2, 130-3, and 130-4.

According to the user's preference, each of the first through n-th aroma capsules 130-1, 130-2, 130-3, and 130-4 installed on the main body 110 inside the housing 120 may be replaced with another aroma capsule, which emits an aromatic substance of a different scent, among the plurality of aroma capsules.

In addition, the aroma diffusing device 100 may include first through n-th fans 140-1, 140-2, 140-3, and 140-4 that are installed on the main body 110 inside the housing 120.

The first through n-th fans 140-1, 140-2, 140-3, and 140-4 may be installed in areas adjacent to the first through n-th aroma capsules 130-1, 130-2, 130-3, and 130-4, respectively.

For example, as illustrated in FIG. 2, the first through n-th fans 140-1, 140-2, 140-3, and 140-4 may be installed under the first through n-th aroma capsules 130-1, 130-2, 130-3, and 130-4, respectively.

Therefore, as a rotation speed of each of the first through n-th fans 140-1, 140-2, 140-3, and 140-4 increases, an intensity of the emission of the aromatic substance of the first through n-th aroma capsules 130-1, 130-2, 130-3, and 130-4 may increase. On the other hand, as the rotation speed of each of the first through n-th fans 140-1, 140-2, 140-3, and 140-4 decreases, the intensity of the emission of the aromatic substance of the first through n-th aroma capsules 130-1, 130-2, 130-3, and 130-4 may decrease.

Although FIG. 2 illustrates that four aroma capsules 130-1, 130-2, 130-3, and 130-4 and four fans 140-1, 140-2, 140-3, and 140-4 are installed on the main body 110 inside the housing 120 as an example, example embodiments are not limited thereto. According to example embodiments, any number of aroma capsules and any number of fans may be installed on the main body 110 inside the housing 120.

In some example embodiments, the housing 120 may include a plurality of openings 121.

For example, as illustrated in FIG. 2, the plurality of openings 121 may be formed on the upper surface of the housing 120.

The aromatic substances emitted from the first through n-th aroma capsules 130-1, 130-2, 130-3, and 130-4 may be diffused to the outside of the aroma diffusing device 100 through the plurality of openings 121 formed on the housing 120.

A circuit board CB 150, which controls an operation of the aroma diffusing device 100, may be included in the main body 110.

For example, the wireless communication module, which performs a wireless communication with the mobile device 200, and a control module, which controls the rotation speed of each of the first through n-th fans 140-1, 140-2, 140-3, and 140-4, may be mounted on the circuit board 150.

According to example embodiments, a lighting module, such as a light emitting diode (LED) module, may be further mounted on the circuit board 150.

Although an example embodiment of the aroma diffusing device 100 is described above with reference to FIG. 2, a shape of the aroma diffusing device 100 illustrated in FIG. 2 is an example only and example embodiments are not limited thereto. According to example embodiments, the aroma diffusing device 100 may be formed in various shapes.

Referring again to FIG. 1, the mobile device 200 may remotely control an overall operation of the aroma diffusing device 100 through the wireless communication.

For example, the mobile device 200 may independently control the intensity of the emission of the aromatic substance of each of the first through n-th aroma capsules 130-1, 130-2, 130-3, and 130-4, which are installed in the aroma diffusing device 100.

In some example embodiments, the mobile device 200 may control the intensity of the emission of the aromatic substance of each of the first through n-th aroma capsules 130-1, 130-2, 130-3, and 130-4 by digitizing the intensity to an integer value.

The mobile device 200 may transmit first through n-th setting values, which correspond to the intensities of the emission of the aromatic substances of the first through n-th aroma capsules 130-1, 130-2, 130-3, and 130-4, respectively, to the aroma diffusing device 100, and the aroma diffusing device 100 may adjust the intensities of the emission of the aromatic substances of the first through n-th aroma capsules 130-1, 130-2, 130-3, and 130-4 by adjusting the rotation speeds of the first through n-th fans 140-1, 140-2, 140-3, and 140-4 based on the first through n-th setting values, respectively, which are received from the mobile device 200.

Therefore, the mobile device 200 may precisely control a combination of scents diffused from the aroma diffusing device 100.

FIGS. 3 to 6 are diagrams for describing an operation of the aroma diffusing system of FIG. 1.

FIGS. 3 to 6 represents examples of a screen displayed on a display device 210 of the mobile device 200 during an operation of the aroma diffusing system 10.

Hereinafter, the operation of the aroma diffusing system 10 will be described with reference to FIGS. 1 to 6.

In some example embodiments, each of the first through n-th aroma capsules 130-1, 130-2, 130-3, and 130-4 may include an electronic tag storing a kind of a scent of a corresponding aroma capsule. For example, the electronic tag may correspond to a radio frequency identification (RFID) tag.

When the first through n-th aroma capsules 130-1, 130-2, 130-3, and 130-4 are installed in the aroma diffusing device 100, the aroma diffusing device 100 may read first through n-th kinds of scents from the electronic tags included in the first through n-th aroma capsules 130-1, 130-2, 130-3, and 130-4, respectively, and transmit the first through n-th kinds of scents to the mobile device 200.

Figure 3:
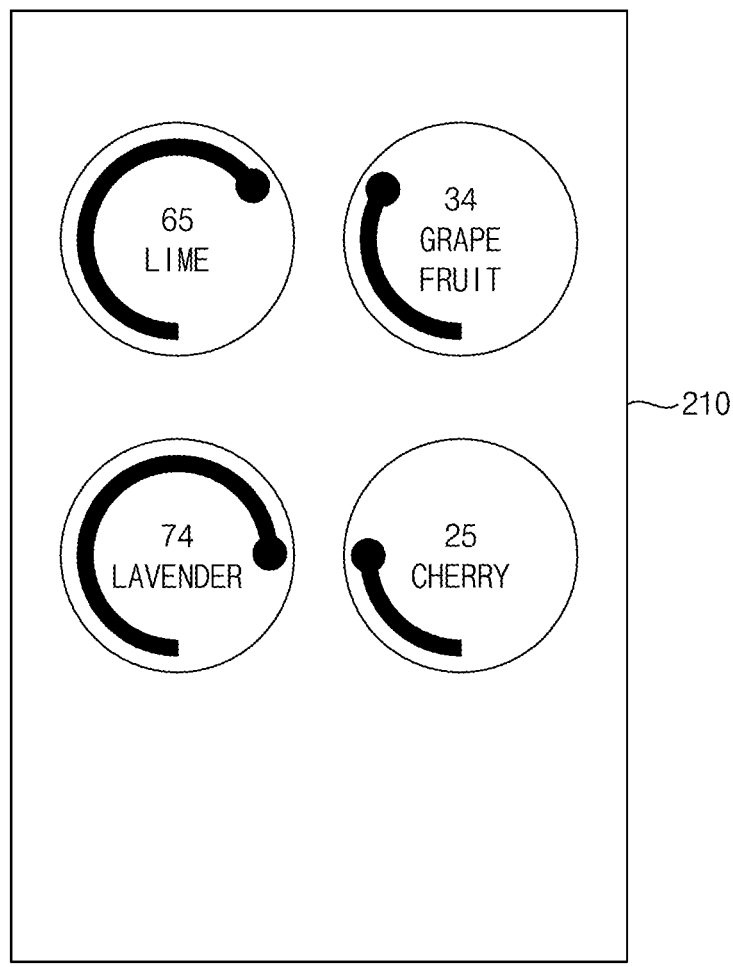
FIGS. 3 to 6 are diagrams for describing an operation of the aroma diffusing system of FIG. 1.

As illustrated in FIG. 3, the mobile device 200 may display the first through n-th kinds of scents of the first through n-th aroma capsules 130-1, 130-2, 130-3, and 130-4, which are received from the aroma diffusing device 100, and the first through n-th setting values that are currently set, which correspond to the intensities of the emission of the aromatic substances of the first through n-th aroma capsules 130-1, 130-2, 130-3, and 130-4, respectively, on the display device 210.

FIG. 3 illustrates an example of a screen displayed on the display device 210 when the first aroma capsule 130-1, which emits an aromatic substance of a lime scent, the second aroma capsule 130-2, which emits an aromatic substance of a grapefruit scent, the third aroma capsule 130-3, which emits an aromatic substance of a cherry scent, and the fourth aroma capsule 130-4, which emits an aromatic substance of a lavender scent are installed in the aroma diffusing device 100, and the first through n-th setting values, which correspond to the intensities of the emission of the aromatic substances of the first through n-th aroma capsules 130-1, 130-2, 130-3, and 130-4, are set to 65, 34, 25, and 74, respectively.

In FIG. 3, the mobile device 200 is illustrated to control the intensity of the emission of the aromatic substance of each of the first through n-th aroma capsules 130-1, 130-2, 130-3, and 130-4 by digitizing the intensity to an integer value equal to or smaller than 100.

The first through n-th setting values may be changed on the mobile device 200 by the user's input. For example, the user may change the first through n-th setting values by providing a tough input or a button input to the mobile device 200.

In this case, the mobile device 200 may transmit the first through n-th setting values that are changed to the aroma diffusing device 100, and the aroma diffusing device 100 may adjust the intensities of the emission of the aromatic substances of the first through n-th aroma capsules 130-1, 130-2, 130-3, and 130-4 by adjusting the rotation speeds of the first through n-th fans 140-1, 140-2, 140-3, and 140-4 based on the first through n-th setting values, respectively, which are received from the mobile device 200.

As described above, since the aroma diffusing system 10 according to example embodiments precisely controls the intensities of the emission of the aromatic substances of the first through n-th aroma capsules 130-1, 130-2, 130-3, and 130-4 based on the user's choice, the aroma diffusing system 10 may provide an accurate combination of scents that the user wants.

For example, when the user is satisfied with the combination of scents diffused from the aroma diffusing device 100, the mobile device 200 may memorize the first through n-th setting values that are currently set, which correspond to the intensities of the emission of the aromatic substances of the first through n-th aroma capsules 130-1, 130-2, 130-3, and 130-4, respectively. When the aroma diffusing device 100 is turned on to operate next time, the mobile device 200 may set the first through n-th setting values, which are memorized before, as the intensities of the emission of the aromatic substances of the first through n-th aroma capsules 130-1, 130-2, 130-3, and 130-4, respectively. In this case, the aroma diffusing device 100 may provide the same combination of scents as before.

Each of the first through n-th aroma capsules 130-1, 130-2, 130-3, and 130-4 may include a certain amount of a respective aromatic substance initially. Therefore, although the rotation speed of each of the first through n-th fans 140-1, 140-2, 140-3, and 140-4 is consistent, an amount of the aromatic substance that is emitted from each of the first through n-th aroma capsules 130-1, 130-2, 130-3, and 130-4 may decrease as a consumption of the aromatic substance of each of the first through n-th aroma capsules 130-1, 130-2, 130-3, and 130-4 increases.

Therefore, the mobile device 200 included in the aroma diffusing system 10 may estimate consumptions of the aromatic substances of the first through n-th aroma capsules 130-1, 130-2, 130-3, and 130-4, and tune the intensities of the emission of the aromatic substances of the first through n-th aroma capsules 130-1, 130-2, 130-3, and 130-4 based on the estimated consumptions of the aromatic substances of the first through n-th aroma capsules 130-1, 130-2, 130-3, and 130-4, respectively.

In some example embodiments, the mobile device 200 may estimate the consumptions of the aromatic substances of the first through n-th aroma capsules 130-1, 130-2, 130-3, and 130-4 based on the first through n-th setting values, respectively.

For example, the mobile device 200 may determine first through n-th consumption indexes, which correspond to the consumptions of the aromatic substances of the first through n-th aroma capsules 130-1, 130-2, 130-3, and 130-4, respectively, by accumulating values generated by multiplying an operation time of the aroma diffusing device 100 by the first through n-th setting values that are set during the operation time, respectively.

Therefore, as the operation time during which a corresponding aroma capsule is operated with a relatively large setting value increases, the consumption index of the corresponding aroma capsule may have a relatively large value. On the other hand, as the operation time during which a corresponding aroma capsule is operated with a relatively large setting value decreases, the consumption index of the corresponding aroma capsule may have a relatively small value.

After that, the mobile device 200 may determine first through n-th compensation values proportional to the first through n-th consumption indexes, respectively, and multiply the first through n-th setting values, which are currently set, by the first through n-th compensation values to generate first through n-th compensated setting values, respectively.

Therefore, when the consumption of the aromatic substance of a corresponding aroma capsule is relatively large, the mobile device 200 may determine the compensated setting value of the corresponding aroma capsule by multiplying the current setting value of the corresponding aroma capsule by a relatively large compensation value. On the other hand, when the consumption of the aromatic substance of a corresponding aroma capsule is relatively low, the mobile device 200 may determine the compensated setting value of the corresponding aroma capsule by multiplying the current setting value of the corresponding aroma capsule by a relatively small compensation value.

The mobile device 200 may transmit the first through n-th compensated setting values to the aroma diffusing device 100, and the aroma diffusing device 100 may adjust the intensities of the emission of the aromatic substances of the first through n-th aroma capsules 130-1, 130-2, 130-3, and 130-4 based on the first through n-th compensated setting values, respectively, which are received from the mobile device 200.

As described above, the mobile device 200 included in the aroma diffusing system 10 may estimate the consumptions of the aromatic substances of the first through n-th aroma capsules 130-1, 130-2, 130-3, and 130-4, and tune the intensities of the emission of the aromatic substances of the first through n-th aroma capsules 130-1, 130-2, 130-3, and 130-4 based on the estimated consumptions of the aromatic substances of the first through n-th aroma capsules 130-1, 130-2, 130-3, and 130-4, respectively.

Therefore, the aroma diffusing system 10 may provide the same combination of scents for the same combination of the first through n-th setting values regardless of the consumptions of the aromatic substances of the first through n-th aroma capsules 130-1, 130-2, 130-3, and 130-4.

In some example embodiments, the aroma diffusing system 10 may include a scent recommendation function.

Hereinafter, the scent recommendation function of the aroma diffusing system 10 will be described with reference to FIG. 4.

Whenever the aroma diffusing device 100 is turned on to operate, the mobile device 200 may cumulatively store the first through n-th kinds of scents of the first through n-th aroma capsules 130-1, 130-2, 130-3, and 130-4, which are installed in the aroma diffusing device 100, and the first through n-th setting values in relation with at least one of a current time, a current season, and a current weather as a user data. According to example embodiments, the mobile device 200 may store the user data in an internal storage device or in an external server.

Therefore, the user data may include information about which combination of scents are selected by the user under a certain time or a certain weather.

The user may select the scent recommendation function on the mobile device 200.

Figure 4:
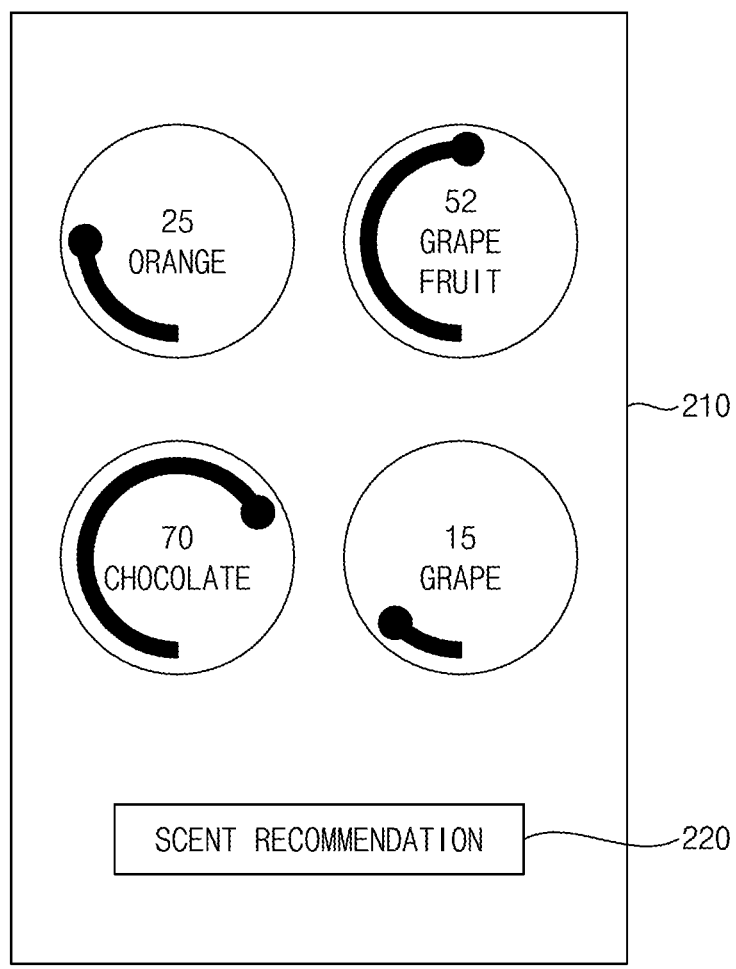

For example, as illustrated in FIG. 4, the user may select the scent recommendation function by touch a scent recommendation button 220 displayed on the display device 210 of the mobile device 200.

In this case, the mobile device 200 may perform a data mining on the user data to determine first through n-th recommended kinds of scents and first through n-th recommended setting values of the first through n-th recommended kinds of scents, which are matched with at least one of a time, a season, and a weather at a moment of the selection of the scent recommendation function.

For example, the mobile device 200 may determine the first through n-th recommended kinds of scents and the first through n-th recommended setting values that are most appropriate for the user at the moment of the selection of the scent recommendation function based on the kinds of scents and the setting values of the kinds of scents that are selected at a time, a season, or a weather similar to those at the moment of the selection of the scent recommendation function.

The mobile device 200 may display the first through n-th recommended kinds of scents and the first through n-th recommended setting values on the display device 210.

FIG. 4 illustrates an example of a screen displayed on the display device 210 when the first through n-th recommended kinds of scents are determined as an orange scent, a grapefruit scent, a grape scent, and a chocolate scent and the first through n-th recommended setting values of the first through n-th recommended kinds of scents are determined as 25, 52, 15, and 70.

After that, the mobile device 200 may determine whether the first through n-th kinds of scents of the first through n-th aroma capsules 130-1, 130-2, 130-3, and 130-4, which are installed in the aroma diffusing device 100, are the same as the first through n-th recommended kinds of scents.

When the first through n-th kinds of scents of the first through n-th aroma capsules 130-1, 130-2, 130-3, and 130-4, which are installed in the aroma diffusing device 100, are the same as the first through n-th recommended kinds of scents, the mobile device 200 may transmit the first through n-th recommended setting values to the aroma diffusing device 100, and the aroma diffusing device 100 may adjust the intensities of the emission of the aromatic substance of the first through n-th aroma capsules 130-1, 130-2, 130-3, and 130-4 based on the first through n-th recommended setting values, respectively, which are received from the mobile device 200.

On the other hand, when the first through n-th kinds of scents of the first through n-th aroma capsules 130-1, 130-2, 130-3, and 130-4, which are installed in the aroma diffusing device 100, are different from the first through n-th recommended kinds of scents, the mobile device 200 may display an aroma capsule replacement message on the display device 210. The aroma capsule replacement message may include a list of the first through n-th recommended kinds of scents.

When the user replaces the first through n-th aroma capsules 130-1, 130-2, 130-3, and 130-4, which are installed in the aroma diffusing device 100, with the aroma capsules corresponding to the first through n-th recommended kinds of scents according to the aroma capsule replacement message, the mobile device 200 may transmit the first through n-th recommended setting values to the aroma diffusing device 100, and the aroma diffusing device 100 may adjust the intensities of the emission of the aromatic substance of the first through n-th aroma capsules 130-1, 130-2, 130-3, and 130-4 based on the first through n-th recommended setting values, respectively, which are received from the mobile device 200.

As described above with reference to FIG. 4, the aroma diffusing system 10 according to example embodiments may provide the combination of scents corresponding to the first through n-th setting values that are set by the user, and moreover, when the scent recommendation function is selected, the aroma diffusing system 10 may provide the most appropriate combination of scents for the user by analyzing a scent preference of the user according to a time, a season, and a weather.

In some example embodiments, the aroma diffusing system 10 may include a scent storage function.

Hereinafter, the scent storage function of the aroma diffusing system 10 will be described with reference to FIGS. 5 and 6.

Figure 5:
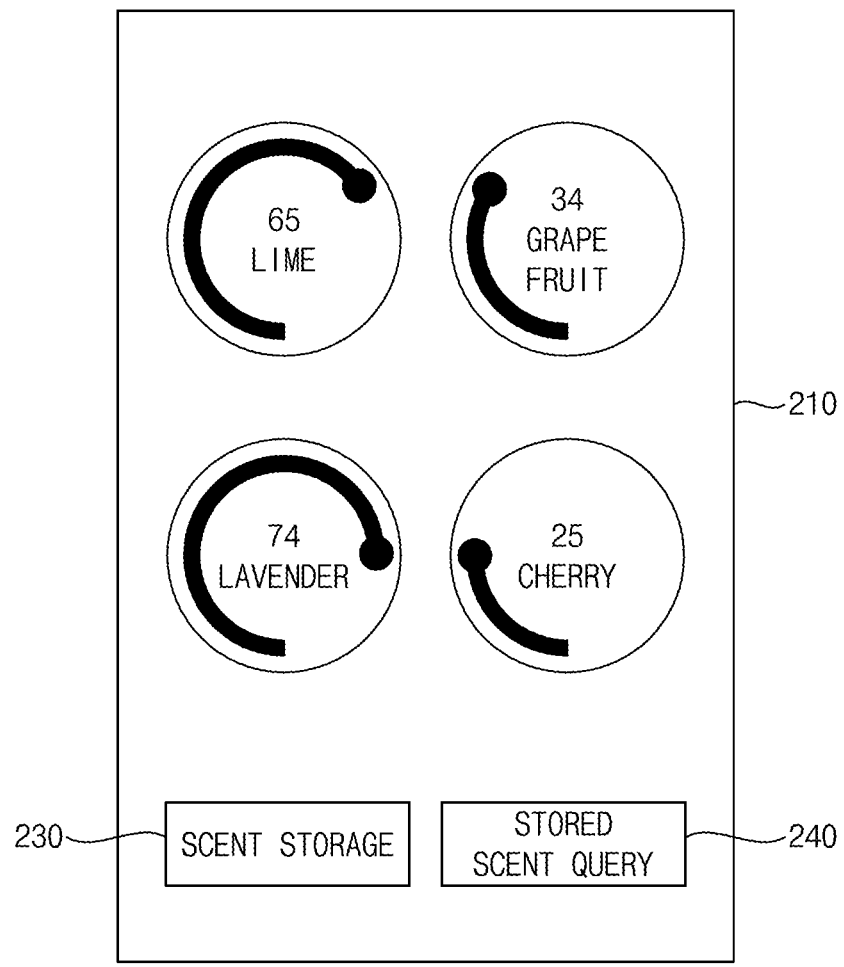

FIG. 5 illustrates an example of a screen displayed on the display device 210 when the first aroma capsule 130-1, which emits an aromatic substance of a lime scent, the second aroma capsule 130-2, which emits an aromatic substance of a grapefruit scent, the third aroma capsule 130-3, which emits an aromatic substance of a cherry scent, and the fourth aroma capsule 130-4, which emits an aromatic substance of a lavender scent are installed in the aroma diffusing device 100, and the first through n-th setting values, which correspond to the intensities of the emission of the aromatic substances of the first through n-th aroma capsules 130-1, 130-2, 130-3, and 130-4, are set to 65, 34, 25, and 74, respectively.

When the user is satisfied with the combination of scents diffused from the aroma diffusing device 100 currently, the user may select the scent storage function on the mobile device 200.

For example, as illustrated in FIG. 5, the user may select the scent storage function by touch a scent storage button 230 displayed on the display device 210 of the mobile device 200.

In this case, the mobile device 200 may display a screen for receiving information about the combination of scents to be stored from the user on the display device 210.

Figure 6:
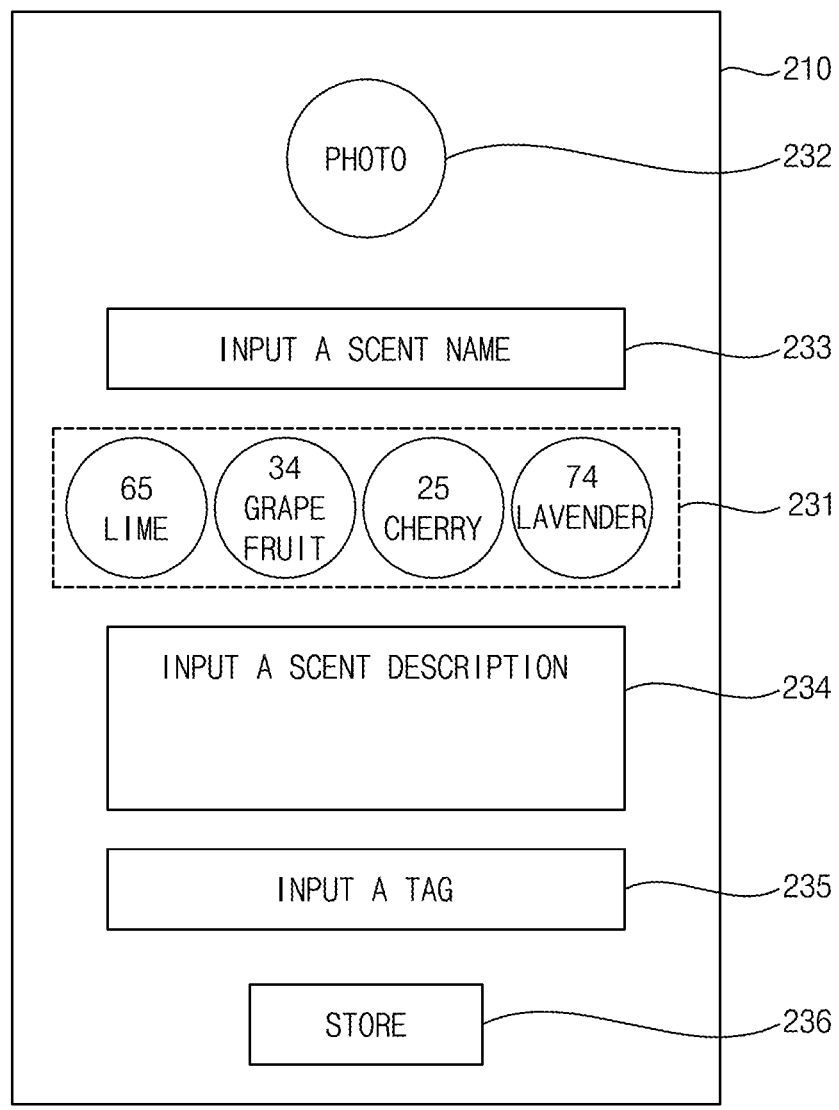

For example, as illustrated in FIG. 6, the mobile device 200 may display the first through n-th kinds of scents of the first through n-th aroma capsules 130-1, 130-2, 130-3, and 130-4, which are installed in the aroma diffusing device 100, and the first through n-th setting values, which are currently set, in an area 231 of the display device 210.

In addition, the mobile device 200 may display a photo input box 232 that receives a photo to be related with the current combination of scents, which are diffused from the aroma diffusing device 100 currently, a scent name input box 233 that receives a scent name of the current combination of scents, a scent description input box 234 that receives a scent description of the current combination of scents or a user's feeling for the current combination of scents, and a tag input box 235 that receives a tag to be related with the current combination of scents for searching on the display device 210.

In some example embodiments, the scent name may be a mandatory input item and the photo, the scent description, and the tag may be optional input items.

When the user touches a store button 236 after inputting the various items about the current combination of scents, the mobile device 200 may store the first through n-th kinds of scents of the first through n-th aroma capsules 130-1, 130-2, 130-3, and 130-4, which are installed in the aroma diffusing device 100, and the first through n-th setting values, which are currently set, in relation with the scent name, the photo, the scent description, and the tag, which are input by the user, in the internal storage device as a stored scent.

In addition, the user may select a stored scent query function in the mobile device 200 to query the stored scents, which are stored in the internal storage device, and to enjoy one of the stored scents.

For example, as illustrated in FIG. 5, the user may select the stored scent query function by touch a stored scent query button 240 displayed on the display device 210 of the mobile device 200.

In this case, the mobile device 200 may display a list of the stored scents, which are stored in the internal storage device, on the display device 210, and the user may select one of the stored scents among the list of the stored scents displayed on the display device 210.

After that, the mobile device 200 may determine whether the first through n-th kinds of scents of the first through n-th aroma capsules 130-1, 130-2, 130-3, and 130-4, which are installed in the aroma diffusing device 100, are the same as the first through n-th kinds of scents corresponding to a selected stored scent, which is selected by the user among the list of the stored scents.

When the first through n-th kinds of scents of the first through n-th aroma capsules 130-1, 130-2, 130-3, and 130-4, which are installed in the aroma diffusing device 100, are the same as the first through n-th kinds of scents corresponding to the selected stored scent, the mobile device 200 may transmit the first through n-th setting values corresponding to the selected stored scent to the aroma diffusing device 100, and the aroma diffusing device 100 may adjust the intensities of the emission of the aromatic substance of the first through n-th aroma capsules 130-1, 130-2, 130-3, and 130-4 based on the first through n-th setting values, respectively, which are received from the mobile device 200.

On the other hand, when the first through n-th kinds of scents of the first through n-th aroma capsules 130-1, 130-2, 130-3, and 130-4, which are installed in the aroma diffusing device 100, are different from the first through n-th kinds of scents corresponding to the selected stored scent, the mobile device 200 may display an aroma capsule replacement message on the display device 210. The aroma capsule replacement message may include a list of the first through n-th kinds of scents corresponding to the selected stored scent.

When the user replaces the first through n-th aroma capsules 130-1, 130-2, 130-3, and 130-4, which are installed in the aroma diffusing device 100, with the aroma capsules corresponding to the first through n-th kinds of scents of the selected stored scent according to the aroma capsule replacement message, the mobile device 200 may transmit the first through n-th setting values corresponding to the selected stored scent to the aroma diffusing device 100, and the aroma diffusing device 100 may adjust the intensities of the emission of the aromatic substance of the first through n-th aroma capsules 130-1, 130-2, 130-3, and 130-4 based on the first through n-th setting values, respectively, which are received from the mobile device 200.

As described above with reference to FIGS. 5 and 6, since the aroma diffusing system 10 according to example embodiments stores the combination of scents that the user prefers and provides the same combination of scents as before by selecting one of the stored scents, the aroma diffusing system 10 may provide an increased convenience to the user.

Figure 7:
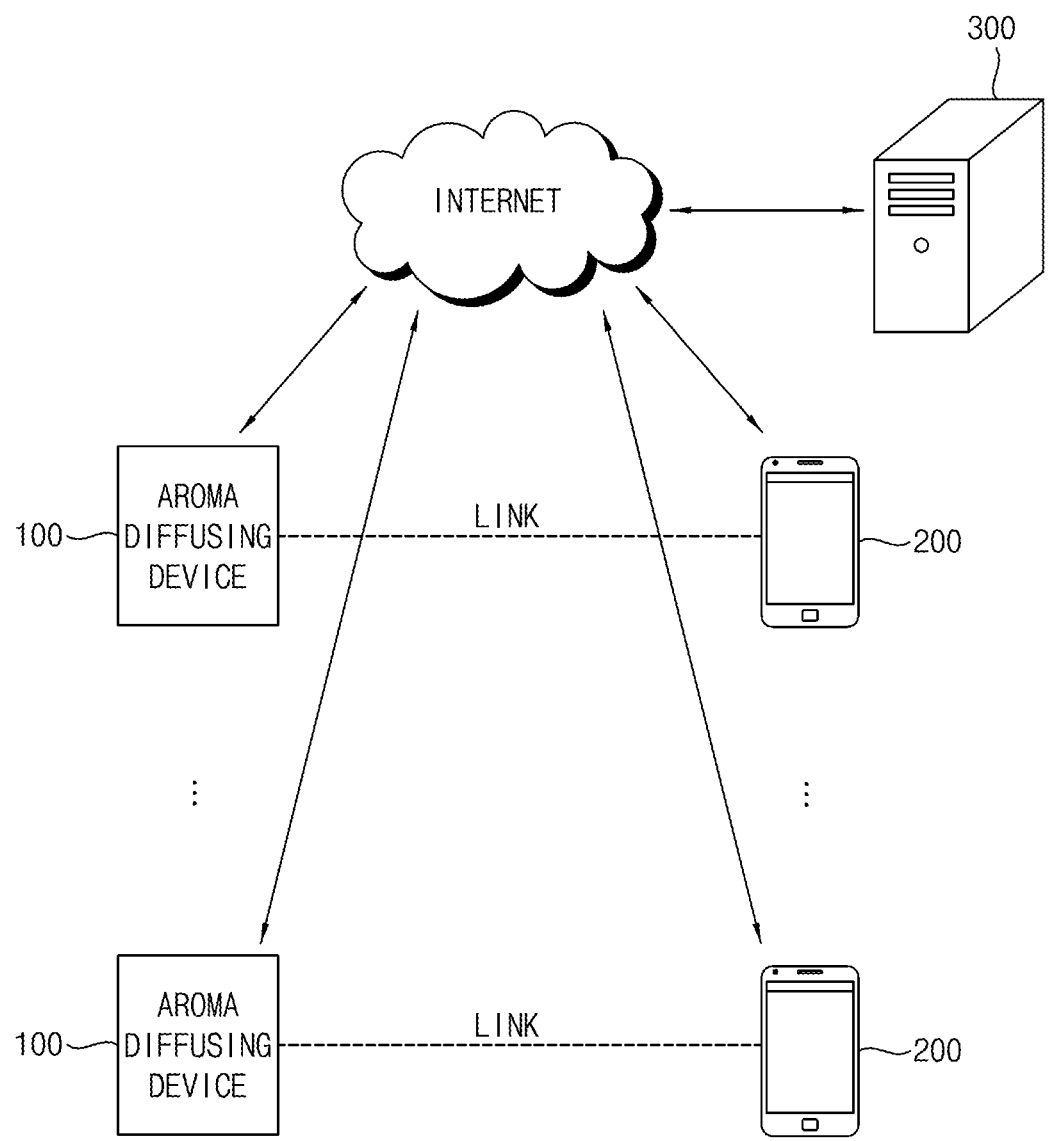
FIG. 7 is a diagram illustrating an aroma diffusing system according to other example embodiments.

FIG. 7 is a diagram illustrating an aroma diffusing system according to other example embodiments.

Referring to FIG. 7, an aroma diffusing system 20 includes a plurality of aroma diffusing devices 100, a plurality of mobile devices 200, and an aroma sharing server 300.

The plurality of aroma diffusing devices 100 may communicate with the plurality of mobile devices 200, respectively, through a wireless communication.

For example, the wireless communication may correspond to an internet.

Each of a plurality of users may control his own aroma diffusing device 100 using his own mobile device 200.

Each of the plurality of aroma diffusing devices 100 included in the aroma diffusing system 20 of FIG. 7 may be implemented with the aroma diffusing device 100 included in the aroma diffusing system 10 of FIG. 1.

In addition, each of the plurality of mobile devices 200 included in the aroma diffusing system 20 of FIG. 7 may be implemented with the mobile device 200 included in the aroma diffusing system 10 of FIG. 1.

Structures and operations of the mobile devices 200 and the aroma diffusing devices 100 connected to the mobile devices 200 are described above with reference to FIGS. 1 to 6. Therefore, duplicated description about the plurality of aroma diffusing devices 100 and the plurality of mobile devices 200 included in the aroma diffusing system 20 of FIG. 7 will be omitted here, and a scent sharing function provided by the aroma diffusing system 20 will be described hereinafter.

As illustrated in FIG. 7, the aroma sharing server 300 may be connected to the plurality of mobile devices 200 through the internet.

The aroma diffusing system 20 may provide the scent sharing function to the plurality of users using the aroma sharing server 300.

Figure 8:
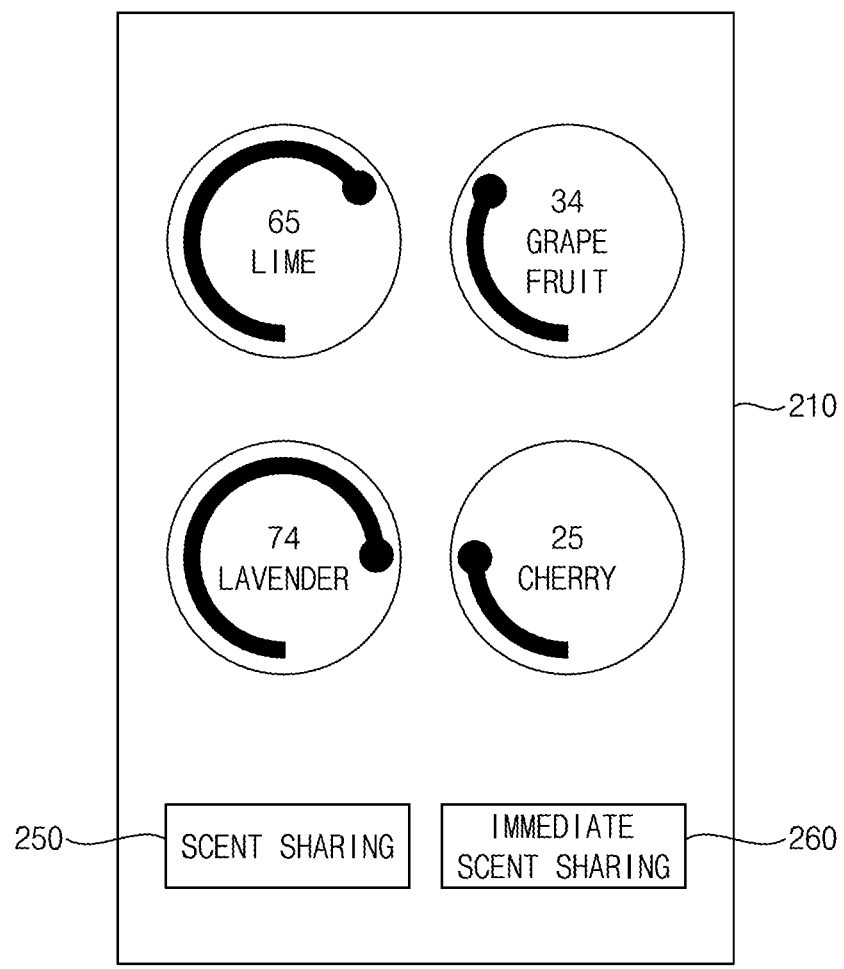
FIG. 8 is a diagram for describing a scent sharing function provided by the aroma diffusing system of FIG. 7.

FIG. 8 is a diagram for describing a scent sharing function provided by the aroma diffusing system of FIG. 7.

Hereinafter, the scent sharing function of the aroma diffusing system 20 will be described with reference to FIGS. 7 and 8.

In some example embodiments, the user may select the scent sharing function on the mobile device 200 regardless of whether the aroma diffusing device 100 is turned on or turned off.

For example, as illustrated in FIG. 8, the user may select the scent sharing function by touch a scent sharing button 250 displayed on the display device 210 of the mobile device 200.

In this case, the mobile device 200 may display the list of the stored scents, which are stored in the internal storage device, on the display device 210, and the user may select one of the stored scents among the list of the stored scents displayed on the display device 210 to be shared with others.

After that, the mobile device 200 may transmit the first through n-th kinds of scents and the first through n-th setting values together with the scent name, the photo, the scent description, and the tag, which correspond to a selected stored scent that is selected by the user among the stored scents, which are stored in the internal storage device, to the aroma sharing server 300 as a shared scent.

In other example embodiments, the user may select an immediate scent sharing function on the mobile device 200 while the aroma diffusing device 100 is turned on to operate.

For example, as illustrated in FIG. 8, the user may select the immediate scent sharing function by touch an immediate scent sharing button 260 displayed on the display device 210 of the mobile device 200.

FIG. 8 illustrates an example of a screen displayed on the display device 210 when the first aroma capsule 130-1, which emits an aromatic substance of a lime scent, the second aroma capsule 130-2, which emits an aromatic substance of a grapefruit scent, the third aroma capsule 130-3, which emits an aromatic substance of a cherry scent, and the fourth aroma capsule 130-4, which emits an aromatic substance of a lavender scent are installed in the aroma diffusing device 100, and the first through n-th setting values, which correspond to the intensities of the emission of the aromatic substances of the first through n-th aroma capsules 130-1, 130-2, 130-3, and 130-4, are set to 65, 34, 25, and 74, respectively.

In this case, as described above with reference to FIG. 6, the mobile device 200 may display a screen for receiving various information about the current combination of scents, which is diffused from the aroma diffusing device 100 currently, on the display device 210, and receive the scent name, the photo, the scent description, and the tag for the current combination of scents from the user's input.

After that, the mobile device 200 may transmit the first through n-th kinds of scents of the first through n-th aroma capsules 130-1, 130-2, 130-3, and 130-4, which are installed in the aroma diffusing device 100, and the first through n-th setting values, which are currently set, together with the scent name, the photo, the scent description, and the tag that is input by the user to the aroma sharing server 300 as the shared scent.

The aroma sharing server 300 may internally stores the shared scents received from the plurality of mobile devices 200.

After that, the aroma sharing server 300 may transmit the shared scents, which are stored internally, to each of the plurality of mobile devices 200, and each of the plurality of mobile devices 200 may display a list of the shared scents received from the aroma sharing server 300 on the display device 210.

Therefore, the user may get a list of the shared scents, which are shared by other users, on his own mobile device 200.

The user may select one of the shared scents displayed on the display device 210 of the mobile device 200.

In this case, the mobile device 200 may determine whether the first through n-th kinds of scents of the first through n-th aroma capsules 130-1, 130-2, 130-3, and 130-4, which are installed in the aroma diffusing device 100, are the same as the first through n-th kinds of scents corresponding to a selected shared scent, which is selected by the user among the list of the shared scents.

When the first through n-th kinds of scents of the first through n-th aroma capsules 130-1, 130-2, 130-3, and 130-4, which are installed in the aroma diffusing device 100, are the same as the first through n-th kinds of scents corresponding to the selected shared scent, the mobile device 200 may transmit the first through n-th setting values corresponding to the selected shared scent to the aroma diffusing device 100, and the aroma diffusing device 100 may adjust the intensities of the emission of the aromatic substance of the first through n-th aroma capsules 130-1, 130-2, 130-3, and 130-4 based on the first through n-th setting values, respectively, which are received from the mobile device 200.

On the other hand, when the first through n-th kinds of scents of the first through n-th aroma capsules 130-1, 130-2, 130-3, and 130-4, which are installed in the aroma diffusing device 100, are different from the first through n-th kinds of scents corresponding to the selected shared scent, the mobile device 200 may display an aroma capsule replacement message on the display device 210. The aroma capsule replacement message may include a list of the first through n-th kinds of scents corresponding to the selected shared scent.

When the user replaces the first through n-th aroma capsules 130-1, 130-2, 130-3, and 130-4, which are installed in the aroma diffusing device 100, with the aroma capsules corresponding to the first through n-th kinds of scents of the selected shared scent according to the aroma capsule replacement message, the mobile device 200 may transmit the first through n-th setting values corresponding to the selected shared scent to the aroma diffusing device 100, and the aroma diffusing device 100 may adjust the intensities of the emission of the aromatic substance of the first through n-th aroma capsules 130-1, 130-2, 130-3, and 130-4 based on the first through n-th setting values, respectively, which are received from the mobile device 200.

In some example embodiments, after the selected shared scent are provided to the user through the aroma diffusing device 100, the mobile device 200 may transmit a recommendation signal for the selected shared scent to the aroma sharing server 300 based on the user's input.

For example, when the mobile device 200 transmits the first through n-th setting values corresponding to the selected shared scent to the aroma diffusing device 100, the mobile device 200 may display a recommendation button on the display device 200. When the user touches the recommendation button on the display device 200, the mobile device 200 may transmit the recommendation signal for the selected shared scent to the aroma sharing server 300.

The aroma sharing server 300 may count a number of the recommendation signals received from the plurality of mobile devices 200 for each of the shared scents, which are stored internally, to determine a preference index for each of the shared scents.

After that, the aroma sharing server 300 may determine shared scents having a relatively high preference index among the shared scents as popular shared scents and transmit the popular shared scents to the plurality of mobile devices 200.

Each of the plurality of mobile devices 200 may display a list of the popular shared scents, which are received from the aroma sharing server 300, on the display device 210.

In this way, the aroma diffusing system 20 may select shared scents, which are recommended by majority of the users, among the shared scents as the popular shared scents and provide the popular shared scents to the users.

As described above with reference to FIGS. 7 and 8, the user may provide the combination of scents, which the user wants to share with other users, to the aroma sharing server 300 as the shared scent, and enjoy the shared scents, which are shared by the other users, easily using the aroma diffusing system 20.

As such, the aroma diffusing system 20 according to example embodiments may provide the combination of scents that the user prefers to the user, and moreover, perform a social network services (SNS) function in which the plurality of users share preferred combinations of scents with each other. Therefore, the aroma diffusing system 20 may provide an increased satisfaction to the user.

The foregoing is illustrative of various example embodiments and is not to be construed as limited to the specific example embodiments disclosed and the figures attached, those skilled in the art will readily appreciate that many modifications are possible in the example embodiments without materially departing from the novel teachings and advantages of the present inventive concept, and the modifications to the disclosed example embodiments, as well as other example embodiments, are intended to be included within the scope of the appended claims.

DESCRIPTION OF REFERENCE NUMERALS 10, 20: an aroma diffusing system
100: an aroma diffusing device
110: a main body
120: a housing
121: an opening
130: an aroma capsule
140: a fan
150: a circuit board
200: a mobile device
210: a display device

The invention claimed is:

1. An aroma diffusing system, comprising:
an aroma diffusing device including a wireless communication module, the aroma diffusing device being equipped with first through n-th aroma capsules selected among a plurality of aroma capsules, which emit respective aromatic substances having different scents from each other, n being an integer equal to or greater than two; and
a mobile device connected to the aroma diffusing device through a wireless communication, the mobile device being configured to independently control an intensity of the emission of the aromatic substance of each of the first through n-th aroma capsules, which are installed in the aroma diffusing device, to determine a combination of scents diffused from the aroma diffusing device,
wherein the mobile device controls the intensity of the emission of the aromatic substance of each of the first through n-th aroma capsules by digitizing the intensity to an integer value,
wherein each of the first through n-th aroma capsules includes an electronic tag storing a kind of a scent of a corresponding aroma capsule,
wherein the aroma diffusing device reads first through n-th kinds of scents from the electronic tags included in the first through n-th aroma capsules, respectively, and transmits the first through n-th kinds of scents to the mobile device, and
wherein the mobile device displays the first through n-th kinds of scents of the first through n-th aroma capsules, which are received from the aroma diffusing device, and first through n-th setting values that are currently set, which correspond to the intensities of the emission of the aromatic substances of the first through n-th aroma capsules, respectively,
wherein, when the first n-th setting values are changed on the mobile device by a user's input, the mobile device transmits the first through n-th setting values that are changed to the aroma diffusing device, and the aroma diffusing device adjusts the intensities of the emission of the aromatic substances of the first through n-th aroma capsules based on the first through n-th setting values, respectively, which are received from the mobile device,
wherein the mobiles device determines first through n-th consumption indexes, which correspond to consumptions of the aromatic substances of the first through n-th aroma capsules, respectively, based on the first through n-th setting values, determines first through n-th compensation values based upon the first through n-th consumption indexes, respectively, multiplies the first through n-th setting values, which are currently set, by the first through n-th compensation values to generate first through n-th compensated setting values, respectively, and transmits the first through n-th compensated setting values to the aroma diffusing device, and wherein the aroma diffusing device adjusts the intensities of the emission of the aromatic substance of the first through n-th aroma capsules based on the first through n-th compensated setting values, respectively, which are received from the mobile device, wherein the mobile device determines the first through n-th consumption indexes by accumulating values generated by multiplying an operation time of the aroma diffusing device by the first through n-th setting values that are set during the operation time, respectively.

2. The aroma diffusing system of claim 1, wherein the aroma diffusing device further includes first through n-th fans corresponding to the first through n-th aroma capsules, respectively, and adjusts the intensities of the emission of the aromatic substances of the first through n-th aroma capsules by adjusting rotation speeds of the first through n-th fans based on the first through n-th setting values, respectively, which are received from the mobile device.

3. The aroma diffusing system of claim 1, wherein, when the aroma diffusing device is turned on to operate, the mobile device cumulatively stores the first through n-th kinds of scents of the first through n-th aroma capsules, which are installed in the aroma diffusing device, and the first through n-th setting values in relation with at least one of a current time, a current season, and a current weather as a user data, and wherein, when a scent recommendation function is selected on the mobile device by the user, the mobile device examines the user data to determine first through n-th recommended kinds of scents and first through n-th recommended setting values of the first through n-th recommended kinds of scents, which are matched with at least one of a time, a season, and a weather at a moment of the selection of the scent recommendation function, and displays the first through n-th recommended kinds of scents and the first through n-th recommended setting values.

4. The aroma diffusing system of claim 3, wherein, when the first through n-th kinds of scents of the first through n-th aroma capsules, which are installed in the aroma diffusing device, are the same as the first through n-th recommended kinds of scents, the mobile device transmits the first through n-th recommended setting values to the aroma diffusing device, and the aroma diffusing device adjusts the intensities of the emission of the aromatic substance of the first through n-th aroma capsules based on the first through n-th recommended setting values, respectively, which are received from the mobile device.

5. The aroma diffusing system of claim 3, wherein, when the first through n-th kinds of scents of the first through n-th aroma capsules, which are installed in the aroma diffusing device, are different from the first through n-th recommended kinds of scents, the mobile device displays an aroma capsule replacement message.

6. An aroma diffusing system, comprising:
an aroma diffusing device including a wireless communication module, the aroma diffusing device being equipped with first through n-th aroma capsules selected among a plurality of aroma capsules, which emit respective aromatic substances having different scents from each other, n being an integer equal to or greater than two; and a mobile device connected to the aroma diffusing device through a wireless communication, the mobile device being configured to independently control an intensity of the emission of the aromatic substance of each of the first through n-th aroma capsules, which are installed in the aroma diffusing device, to determine a combination of scents diffused from the aroma diffusing device;

an aroma sharing server connected to the mobile device through an internet, wherein, when a scent sharing function is selected on the mobile device by the user, the mobile device transmits the first through n-th kinds of scents and the first through n-th setting values together with the scent name, which corresponds to a selected stored scent that is selected by the user among the stored scents, which are stored in an internal storage device, to the aroma sharing server as a shared scent, and the aroma sharing server internally stores the shared scent received from the mobile device, wherein the mobile device controls the intensity of the emission of the aromatic substance of each of the first through n-th aroma capsules by digitizing the intensity to an integer value, wherein each of the first through n-th aroma capsules includes an electronic tag storing a kind of a scent of a corresponding aroma capsule, wherein the aroma diffusing device reads first through n-th kinds of scents from the electronic tags included in the first through n-th aroma capsules, respectively, and transmits the first through n-th kinds of scents to the mobile device, wherein, when a scent storage function is selected on the mobile device by a user, the mobile device stores the first through n-th kinds of scents of the first through n-th aroma capsules, which are installed in the aroma diffusing device, and the first through n-th setting values, which are currently set, in relation with a scent name that is input by the user in the internal storage device as a stored scent, whrein the aroma sharing server transmits shared scents recevied fom other mobile devices to the mobile device, and the mobile device displays a list of the shared scents received from the aroma sharing server, wherein the mobile device transmits a recommendation signal for at least one of the shared scents to the aroma sharing server based on the user's input, and wherein the aroma sharing server counts a number of the recommendation signals received from the mobile device and the other mobile devices for each of the shared scents to determine a preference index for each of the shared scents, determines shared scents having a relatively high preference index among the shared scents as popular shared scents, and transmits the popular shared scents to the mobile device.

7. The aroma diffusing system of claim 6, wherein, when a stored scent query function is selected on the mobile device by the user, the mobile device displays a list of the stored scents stored in the internal storage device.

8. The aroma diffusing system of claim 7, wherein, when the first through n-th kinds of scents of the first through n-th aroma capsules, which are installed in the aroma diffusing device, are the same as the first through n-th kinds of scents corresponding to a selected stored scent, which is selected by the user among the list of the stored scents, the mobile device transmits the first through n-th setting values corresponding to the selected stored scent to the aroma diffusing device, and the aroma diffusing device adjusts the intensities of the emission of the aromatic substance of the first through n-th aroma capsules based on the first through n-th setting values, respectively, which are received from the mobile device.

9. The aroma diffusing system of claim 7, wherein, when the first through n-th kinds of scents of the first through n-th aroma capsules, which are installed in the aroma diffusing device, are different from the first through n-th kinds of scents corresponding to a selected stored scent, which is selected by the user among the list of the stored scents, the mobile device displays an aroma capsule replacement message.

10. The aroma diffusing system of claim 6, wherein, when an immediate scent sharing function is selected on the mobile device by the user, the mobile device transmits the first through n-th kinds of scents of the first through n-th aroma capsules, which are installed in the aroma diffusing device, and the first through n-th setting values, which are currently set, together with a scent name that is input by the user to the aroma sharing server as the shared scent.

11. The aroma diffusing system of claim 6, wherein, when the first through n-th kinds of scents of the first through n-th aroma capsules, which are installed in the aroma diffusing device, are the same as the first through n-th kinds of scents corresponding to a selected shared scent, which is selected by the user among the list of the shared scents, the mobile device transmits the first through n-th setting values corresponding to the selected shared scent to the aroma diffusing device, and the aroma diffusing device adjusts the intensities of the emission of the aromatic substance of the first through n-th aroma capsules based on the first through n-th setting values, respectively, which are received from the mobile device.

12. The aroma diffusing system of claim 6, wherein, when the first through n-th kinds of scents of the first through n-th aroma capsules, which are installed in the aroma diffusing device, are different from the first through n-th kinds of scents corresponding to a selected shared scent, which is selected by the user among the list of the shared scents, the mobile device displays an aroma capsule replacement message.

* * * * *